(12) United States Patent
Zhang et al.

(10) Patent No.: US 11,173,059 B2
(45) Date of Patent: Nov. 16, 2021

(54) TUBE STENT

(71) Applicant: LIFETECH SCIENTIFIC (SHENZHEN) CO., LTD, Shenzhen (CN)

(72) Inventors: Deyuan Zhang, Shenzhen (CN); Chang Shu, Shenzhen (CN); Benhao Xiao, Shenzhen (CN); Yifei Wang, Shenzhen (CN)

(73) Assignee: LIFETECH SCIENTIFIC (SHENZHEN) CO., LTD, Shenzhen (CN)

( * ) Notice: Subject to any disclaimer, the term of this patent is extended or adjusted under 35 U.S.C. 154(b) by 4 days.

(21) Appl. No.: 16/641,759

(22) PCT Filed: Aug. 22, 2018

(86) PCT No.: PCT/CN2018/101762
§ 371 (c)(1),
(2) Date: Feb. 25, 2020

(87) PCT Pub. No.: WO2019/042203
PCT Pub. Date: Mar. 7, 2019

(65) Prior Publication Data
US 2020/0390574 A1    Dec. 17, 2020

(30) Foreign Application Priority Data
Aug. 28, 2017   (CN) .......................... 201710749699.5

(51) Int. Cl.
*A61F 2/82*    (2013.01)
*A61F 2/86*    (2013.01)
(Continued)

(52) U.S. Cl.
CPC ............ *A61F 2/915* (2013.01); *A61F 2/0077* (2013.01); *A61F 2/82* (2013.01); *A61F 2/86* (2013.01);
(Continued)

(58) Field of Classification Search
CPC ...... A61F 2/82; A61F 2/86; A61F 2/89; A61F 2/0077; A61F 2/90; A61F 2/915;
(Continued)

(56) References Cited

U.S. PATENT DOCUMENTS 6,945,991 B1 *   9/2005   Brodeur ..................... A61F 2/07
                                                      623/1.13
2003/0149473 A1 *  8/2003  Chouinard ................ A61F 2/91
                                                      623/1.15
(Continued)

FOREIGN PATENT DOCUMENTS

CN    202554170 U    11/2012
CN    203841853 U     9/2014
(Continued)

OTHER PUBLICATIONS

International Search Report dated Nov. 28, 2018 in corresponding International application No. PCT/CN2018/101762; 4 pages.
(Continued)

*Primary Examiner* — Dinah Baria
(74) *Attorney, Agent, or Firm* — Maier & Maier, PLLC

(57) ABSTRACT

A tube stent includes a first tube body. The first tube body includes a first section, a second section, and a transition section located between the first section and the second section. One end of the transition section is connected to the first section, and the other end is connected to the second section. The shortening rate of the first section and the shortening rate of the second section are smaller than the shortening rate of the transition section. By using the tube
(Continued)

stent, the pulsations of aortas are buffered by the transition section, so that vibration deformations of the tube stent are confined to the first section and the transition section, and accordingly the relative stability of the second section and branch blood vessels can be ensured, and the stimulations to walls of the branch blood vessels can be reduced.

11 Claims, 11 Drawing Sheets

(51) Int. Cl.
  *A61F 2/915*    (2013.01)
  *A61F 2/00*     (2006.01)
(52) U.S. Cl.
  CPC ............... *A61F 2002/91575* (2013.01); *A61F 2250/0029* (2013.01); *A61F 2250/0039* (2013.01)
(58) Field of Classification Search
  CPC .... A61F 2002/91575; A61F 2250/0029; A61F 2250/0039; A61F 2250/0037
  See application file for complete search history.

(56) References Cited

U.S. PATENT DOCUMENTS

| | | |
|---|---|---|
| 2015/0320578 A1 | 11/2015 | Bui et al. |
| 2017/0071768 A1 | 3/2017 | Krieger et al. |

FOREIGN PATENT DOCUMENTS

| | | |
|---|---|---|
| CN | 205144805 U | 4/2016 |
| CN | 106344210 A | 1/2017 |
| EP | 3 090 707 A1 | 11/2016 |
| WO | 2015059019 A1 | 4/2015 |

OTHER PUBLICATIONS

Extended European Search Report dated Apr. 30, 2021, in connection with corresponding EP Application No. 18850981.4; 7 pages.

* cited by examiner

TUBE STENT

FIELD

Embodiments relate to the field of interventional medical instruments, in particular to a tube stent.

BACKGROUND

In the field of treatment of intra-aortic diseases, when an interlayer breach is too close to a branch blood vessel, insufficient anchoring force of an aortic covered stent is easily caused, and a chimney technology or an in-situ windowing technology is generally needed to achieve the purposes of isolating a lesion position and opening the branch blood vessel. Referring to FIG. 1, the chimney technology is such that an aortic covered stent 11 is placed in an aortic lumen and passes over and covers an opening of a branch blood vessel 12 while a branch stent 13 is released in the aortic lumen close to a proximal end of the aortic covered stent 11, so that the proximal end of the branch stent 13 enters the aortic lumen and a distal end of the branch stent 13 enters the branch blood vessel 12, thereby ensuring the blood supply for the branch blood vessel 12. It should be noted that after the stent is implanted into the blood vessel, a blood flow flows from the proximal end of the stent to the distal end of the stent.

A branch stent adopted in the existing chimney technology, however, generally adopts a single raw material specification, and all parts of the branch stent have the same or similar physical properties through a unified processing technology. Although such a stent has good consistency, due to high radial supporting strength of the aortic covered stent, when the branch stent and the aortic covered stent are positioned in the aortic lumen together, the aortic covered stent can generate high squeezing force on the proximal end of the branch stent, and the proximal end of the branch stent has a poor form after being pressed and is easy to deform and even can cause an opening of the proximal end of the branch stent to be completely closed. In addition, when an aortic arch is subjected to the chimney technology, a position, size and form of a blood vessel of the arch part are changed periodically according to the pulsation of blood, the proximal end of the branch stent is attached to the wall of an aorta and thus also moves along with the pulsation of the aorta, while the distal end of the branch stent needs to be attached to the branch blood vessel, and the movement of the branch stent can cause stimulation to the wall of the branch blood vessel and even damage to a branch blood vessel wall. In addition, in the aortic arch, the central axis of the branch blood vessel close to the opening of the aorta and the central axis of the aorta usually form an included angle of 90° or close to 90°, and the branch stent is required to be capable of conforming to the bending of the blood vessel when the chimney technology is carried out. However, the current branch stent is prone to folding or narrowing at a connecting part between the aortic lumen and the branch blood vessel, which affects the patency of the blood flow in the branch blood vessel.

SUMMARY

On such basis, it is desired to provide a tube stent to solve at least one of the above-mentioned technical problems.

A tube stent includes a first tube body, and the first tube body includes a first section, a second section and a transition section which is positioned between the first section and the second section, one end of the transition section is connected with the first section, the other end of the transition section is connected with the second section, and shortening rates of the first section and the second section are less than a shortening rate of the transition section.

According to the tube stent, a shortening rate of the transition section is greater than those of the first section and the second section, and the pulsation of an aorta can be buffered by the transition section, so that the vibration deformation of the tube stent stays at the first section and the transition section, thereby ensuring the relative stability of the second section and a branch blood vessel, and reducing the stimulation to the branch blood vessel wall. Moreover, the first section can be more attached to the aorta wall and an aortic covered stent when released, the possibility of the risk that an opening of the tube stent is covered by the aortic covered stent due to the retraction of a proximal end of the tube stent caused by the flushing of a blood flow is low, and the second section can ensure that a distal end of the tube stent is well anchored in the branch blood vessel.

DETAILED DESCRIPTION

In order to make the purposes, technical solutions, and advantages of the present application more fully apparent, further details are set forth with reference to the accompanying drawings and embodiments. It can be appreciated that the embodiments described herein are merely illustrative and are not intended to be limiting.

In the field of tube stents, a blood flow is defined from a proximal end of a tube stent to a distal end of the tube stent after the tube stent is implanted into a blood vessel.

Hereinafter, technical solutions will be described in further detail with reference to exemplary embodiments.

Embodiment 1

Figure 1:
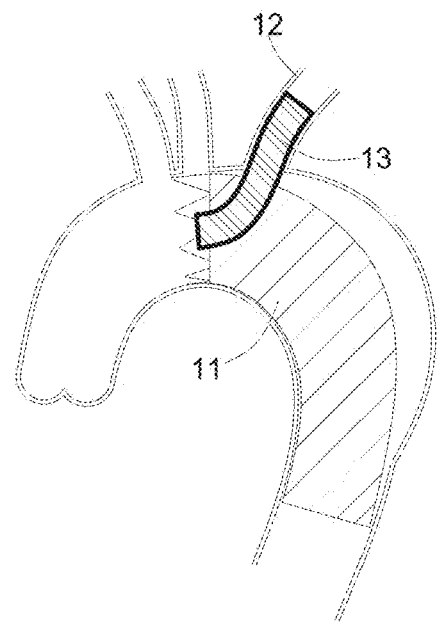
FIG. 1 is a schematic structural view of an aortic covered stent after being implanted into a lumen with a branch stent based on a chimney technology in the prior art.
Figure 2:
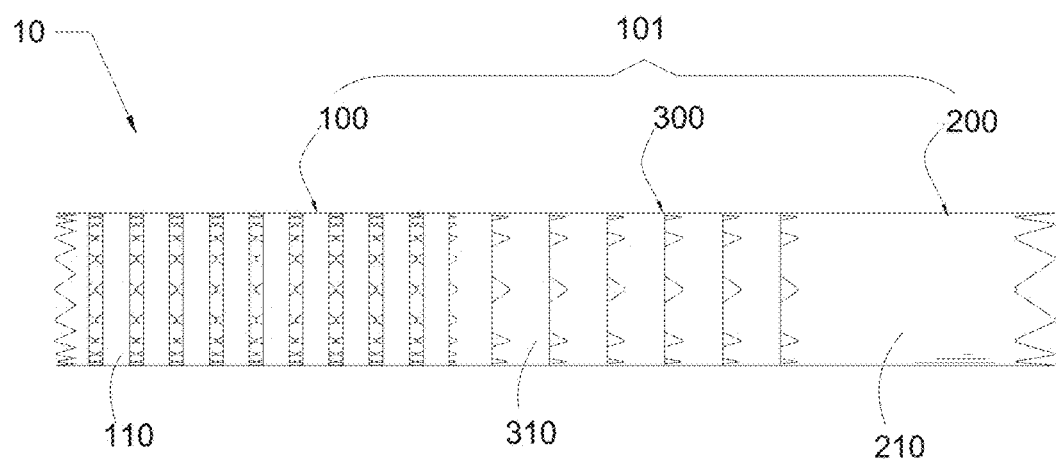
FIG. 2 is a schematic structural view of a tube stent according to a first embodiment.
Figure 3:
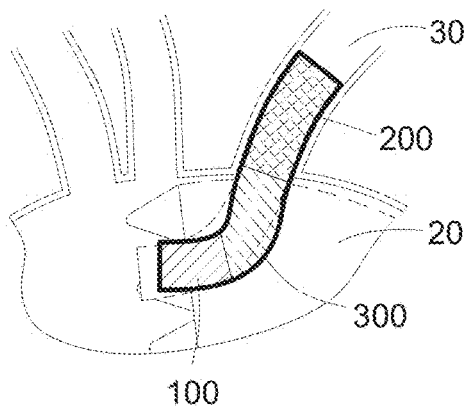
FIG. 3 is a schematic structural view of the tube stent shown in FIG. 2 after being implanted into the lumen with the aortic stent.

Referring to FIG. 2, a tube stent 10 according to an embodiment may be used as a branch stent for a chimney technology, for example, placed in an arterial lumen together with an aortic covered stent. The tube stent 10 includes a first tube body 101, where the first tube body 101 includes a first section 100, a second section 200 and a transition section 300 which is positioned between the first section 100 and the second section 200. One end of the transition section 300 is connected with the first section 100, the other end of the transition section 300 is connected with the second section. The first section 100, the second section 200 and the transition section 300 are of hollow tubular structures. Referring to FIG. 3, after release, the first section 100 is adapted to be placed in an aortic lumen together with the aortic covered stent 20, the second section 200 is adapted to be anchored in a branch blood vessel 30, and the transition section 300 connects the first section 100 and the second section 200 such that the tube stent 10 completes a transition from an aorta to the branch blood vessel by bending deformation of the transition section 300. In one embodiment, the end of the first section 100 is not closer to the branch blood vessel than the end of the aortic covered stent 20. In another embodiment, the end of the first section 100 is further away from the branch blood vessel than the end of the aortic covered stent 20, i.e., the first section 100 extends beyond the end of the aortic covered stent 20, to prevent a situation that a blood flow cannot enter the branch blood vessel through the first section 100 since an opening of the first section 100 is covered by the aortic covered stent and shielded. For example, a length of the first section 100 is not less than 10 mm. In the present embodiment, the length of the first section 100 is not less than 15 mm. The length of the second section 200 is not greater than 40 mm because poor flexibility of the tube stent 10 as a whole is easily caused if the length of the second section 200 is more than 40 mm. In a natural state, the axial length of the transition section 300 is not greater than ¾ of the total length of the first tube body 101 because, if the length of the transition section 300 exceeds ¾ of the total length of the tube stent 10, an overall shortening rate of the tube stent 10 is high, which easily causes displacement of the tube stent 10 upon release.

Further, the radial supporting strength of the first section 100 is greater than the radial supporting strength of the second section 200. For example, when the radial length of the first section 100 is compressed by 50%, the radial supporting strength of the first section 100 is 0.25 N/cm to 5 N/cm, making it difficult for the tube stent 10 to be compressed and deformed in an area where the tube stent is released in parallel with the aortic covered stent, thereby effectively ensuring the supply of the blood flow into the branch blood vessel. In one embodiment, when the radial length of the first section 100 is compressed by 50%, the radial supporting strength of the first section 100 is 0.4 N/cm to 5 N/cm. In this present embodiment, when the radial length of the first section 100 is compressed by 50%, the radial supporting strength of the first section 100 is 1 N/cm to 3 N/cm. When the radial length of the second section 200 is compressed by 50%, the radial supporting strength of the second section 200 is 0.1 N/cm to 1 N/cm.

A radial supporting force can be tested by a flat plate extrusion method, and then the radial supporting strength is calculated with the radial supporting force. For example, the first section 100 is clamped in a tangential direction along the circumference of the first radial supporting structure using two parallel flat plates, with one fixed flat plate fixed to a base and one movable flat plate placed above the first section 100, the two flat plates are always kept parallel during testing, and a radial force is applied to the movable flat plate to test the magnitude of the radial force when the first radial supporting structure is compressed from the original radial length to 50% reduction. The radial supporting strength is equal to the radial force divided by the length of the first section 100.

Further, the flat plate extrusion method described above is only one exemplary testing method and is not intended to limit the present application, and any suitable method may be used by one of ordinary skill in the art to perform an equivalent test to the flat plate extrusion method.

In one embodiment, the shortening rate of the first section 100 is not greater than 10% to avoid the first section 100 from retracting under the impact of the blood flow and an opening of the first section 100 from being shielded by the aortic covered stent, thereby ensuring that the blood flow is able to enter the branch blood vessel from the opening of the first section 100. It is to be noted that, in the present application, the shortening rate means a ratio of a difference value between L and L' to L, where, taking the first section as an example, L is the length of the first section in a natural state, and L' is the length of the first section in the axial direction of the first section remaining constant under the condition that when the two ends of the first section are simultaneously extruded by the force from the ends to the middle, the two ends of the first section draw close to the center middle in the axial direction of the first section, or one end of the first section draws close to the other end of the first section, the included angles between two end surfaces of the first section and the axial direction of the first section are the same as those in the natural state.

Further, the shortening rates of the first section 100 and the second section 200 are less than that of the transition section 300, so that the tube stent 10 can meet the requirement of flexibility to reduce the risk of displacement upon release. In one embodiment, the shortening rate of the transition section 300 is not less than 30%, so that vibration of the proximal end of the tube stent 10 due to fluctuation of the aortic stent can be effectively reduced or absorbed, and displacement of the proximal end of the tube stent 10 due to the vibration can be effectively avoided, thereby ensuring that the second section 200 is relatively stationary with the branch blood vessel and reducing the stimulation of the second section 200 to the branch blood vessel wall. In one embodiment, the shortening rate of the transition section 300 is not greater than 50% to reduce the risk of dislodging upon release of the tube stent 10.

Furthermore, a bending radius of the transition section 300 is not greater than 10 mm, so that the transition section 300 can adapt to various vessels in different forms and is well attached to the vessel wall, the transition section 300 is prevented from folding or narrowing due to the fact that the transition section 300 conforms to the form of the vessel, and the patency of the blood flow of the branch blood vessel is ensured. It is to be noted that the bending diameter of the transition section in the present application means the minimum radius that the transition section can reach under the condition that the variation of the radial length of each part of the transition section is less than 5% on the premise of ensuring the radial form of the transition section when the two ends of the transition section are bent towards the middle. In the present embodiment, the bending radius of the transition section 300 is not greater than 5 mm. It can be noted that the transition section 300 as an entirety may meet the requirements on the shortening rate and the bending radius, where it is possible that the structure of the transition section 300 may be uniform so that the structure may meet the requirements on the shortening rate and the bending radius by modifying the structure of the transition section 300. It also possible that the transition section 300 may be divided into two parts, one part meeting the requirement on the bending radius and the other part meeting the requirement on the shortening rate. For example, a portion of the transition section 300 close to the first section 100 meets the requirement on the bending radius and the portion of the transition section 300 close to the second section 200 meets the requirement on the shortening rate.

Further, the radial length of the first section 100 is not greater than that of the second section 200, so that the difficulty of sheathing the tube stent 10 can be reduced. In this embodiment, the first section 100, the second section 200 and the transition section 300 are all equal in radial length.

Figure 4:
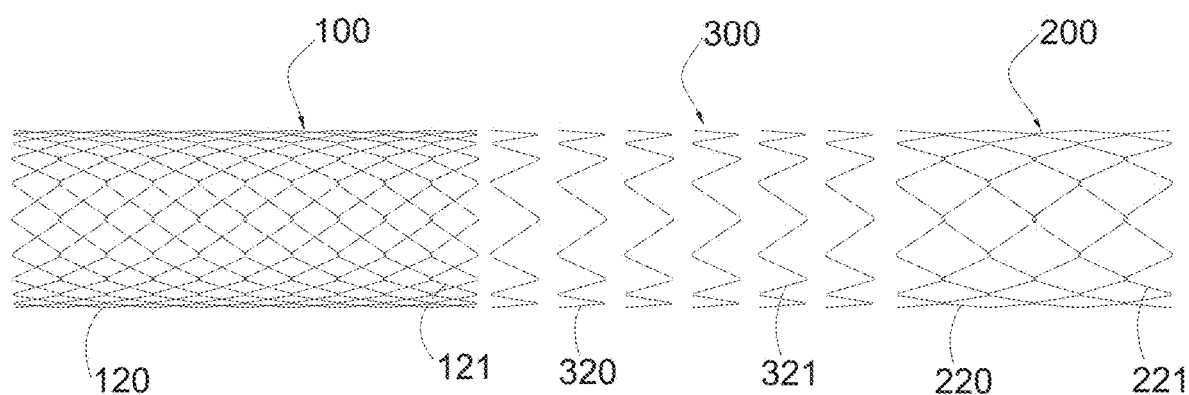
FIG. 4 is a schematic structural view of a bare stent of the tube stent shown in FIG. 2.

The first tube body includes a covering film and a bare stent connected with the covering film. With continuing reference to FIG. 2, the covering film includes a first covering film 110 disposed on the first section 100, a second covering film 210 disposed on the second section 200, and a third covering film 310 disposed on the transition section 300. Referring to FIG. 4 together, the bare stent includes a first radial supporting structure 120 disposed on the first section 100, a second radial supporting structure 220 disposed on the second section 200, and a third radial supporting structure 320 disposed on the transition section 300, where the first radial supporting structure 120 is connected with the first covering film 110, and the second radial supporting structure 220 is connected with the second covering film 210, and the third radial supporting structure 320 is connected with the third covering film 310.

Figure 5:
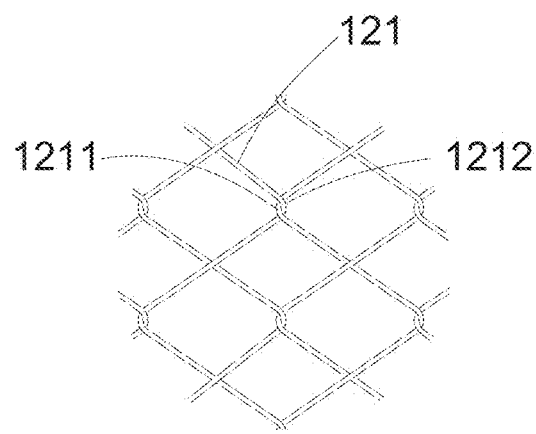
FIG. 5 is a schematic structural view of a first radial supporting structure of a first section of FIG. 4.

With continuing reference to FIG. 4, the first radial supporting structure 120 is woven in a two-layer weaving manner. In one embodiment, the first radial supporting structure 120 includes a mesh structure formed by connecting a number of first wavy rings 121 in the axial direction. Each of the first wavy rings 121 includes 5-20 crests and troughs (i.e., the first wavy ring 121 includes 5-20 crests and 5-20 troughs, with the number of crests and troughs being the same), and a wave height (referring to a vertical height between two adjacent crest and trough of the first wavy ring) of the first wavy ring is 2-5 mm. The number of first wavy rings 121 are arranged in several rows in the axial direction. Each row includes two first wavy rings 121 arranged side by side, in which a number of crests of one first wavy ring 121 correspond one-to-one with a number of troughs of the other wavy ring 121, and a number of rod bodies of one wavy ring 121 are respectively laminated one by one with a number of rod bodies of the other wavy ring 121, so that the two first wavy rings 121 form a number of quadrangles. The crests and troughs of two adjacent rows of the first wavy rings 121 are oppositely arranged, and they are mutually buckled to form an interlocking structure, such that the two adjacent rows of the first wavy rings 121 can get close to each other but cannot get far away from each other, so that the elongation rate of the first section 100 is effectively controlled, and the axial elongation capacity of the first section 100 when the first section 100 is subjected to external force can be reduced, thereby reducing the risk of inaccurate positioning of the first section 100 upon release. Referring to FIG. 5, the interlocking structure is formed in such a manner that wires forming portions of the crests 1211 of the first wavy rings 121 of the right one of the two adjacent rows of the first wavy rings 121 firstly pass over wires forming portions of the troughs 1212 of the first wavy rings 121 of the left one of the two adjacent rows of the first wavy rings 121 so that the wires of the crests and troughs of every two adjacent first wavy rings 121 of the two rows of the first wavy rings 121 are hooked together.

It can be noted that in other embodiments, the first radial supporting structure 120 may also be formed in a three or more layer weaving manner, i.e., each row includes three or more first wavy rings 121 arranged side by side.

The second radial supporting structure 220 is formed in a single-layer weaving manner. A mesh structure of the second radial supporting structure 220 has a greater pore diameter than a mesh structure of the first radial supporting structure 220. In one embodiment, the second radial supporting structure 220 includes a mesh structure formed by connecting a number of second wavy rings 221 in the axial direction. For example, the crests and the troughs of the two adjacent second wavy rings 221 are arranged opposite to each other, and are buckled with each other to form an interlocking structure. In this embodiment, the first wavy rings 121 and the second wavy rings 221 are identical in shape, that is, the numbers of crests and troughs, and the angle between the wave height and a rod body of the second wavy ring 221 are the same as those of the first wavy ring 221, respectively, under which condition, since the weaving density of the second radial supporting structure 220 is less than that of the first radial supporting structure 120 and the pore diameter of the mesh structure of the second radial supporting structure 220 is greater than that of the mesh structure of the first radial supporting structure, the radial supporting strength of the second radial supporting structure 220 is less than that of the first radial supporting structure 120, thereby preventing the proximal end of the tube stent 10 from being extruded and deformed by the aortic stent, and reducing the compression on a branch blood vessel wall by the distal end of the tube stent 10. The third radial supporting structure 320 includes a number of third wavy rings 321 sequentially arranged in the axial direction of the first tube body 101, and two adjacent third wavy rings 321 are independent from each other and are not in contact with each other. In one embodiment, the spacing between the two adjacent third wavy rings 321 (i.e., the distance in the axial direction of the transition section 300 between the trough of one third wavy ring 321 and the crest of the other third wavy ring 321 of the two adjacent third wavy rings 321) is equal. In one embodiment, the spacing between two adjacent third wavy rings 321 is less than the wave height of the third wavy ring 321. In this embodiment, the spacing between two adjacent third wavy rings 321 is 1-4 mm, and the wave height of the third wavy ring 321 is 2-5 mm. The third wavy ring 321 is identical in shape with the first wavy ring 121 or the second wavy ring 221. It can be appreciated that the spacing and the wave height of the third wavy ring can also be adjusted according to the desired shortening rate of the transition section 300.

Figure 6:
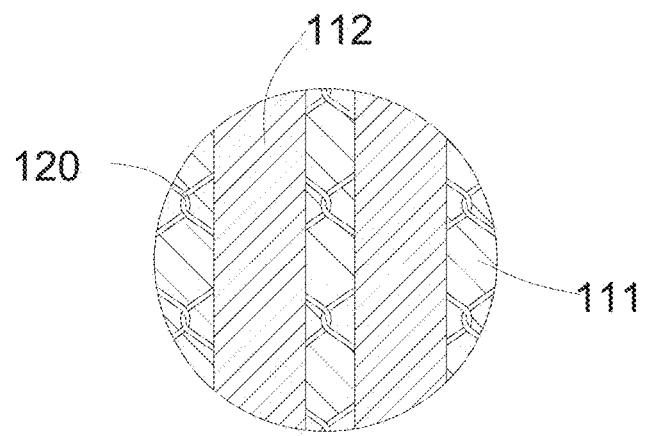
FIG. 6 is a partial schematic structural view of a first covering film of a first section of FIG. 2 matched with the first radial supporting structure.

Referring to FIG. 6, the first covering film 110 includes a first inner film 111 and a number of first outer films 112 attached to the first inner film 111, and the first radial supporting structure 120 is positioned between the first inner film 111 and the number of first outer films 112. For example, the first inner film 111 is of a long cylindrical structure and the first outer films 112 are of short cylindrical structures, i.e., the length of the first inner film 111 in the axial direction of the first radial supporting structure 120 is greater than the lengths of the first outer films 112 in the axial direction of the first radial supporting structure 120, and the first inner film 111 covers an inner wall of the radial supporting structure 121 of the entire first section 100 to isolate the blood flow. The first wavy rings 121 of the first radial supporting structure 120 are sandwiched between the first inner film 111 and the number of first outer films 112 except for the positions of crests and troughs. That is, the entire first inner film 111 covers the inner side of the first radial supporting structure 120, and each first outer film 112 covers middle areas of a row of the first wavy rings 121 except for the positions of crests and troughs. That is, the crest and trough of each of the first wavy rings 121 are exposed, and the other positions are covered by the first inner film 111 and the first outer film 112. Since the crests and troughs of each of the wavy rings 121 are exposed, the crests of each of the first wave-shaped rings 121 can be separated from the first inner film 111 and the first outer film 112 (that is, the crests of each of the first wavy rings 121 can be tilted with respect to the first inner film 111 and the first outer films 112), and the characteristic that the two adjacent first wavy rings 121 in the first radial supporting structure 120 are close to each other can be exerted, thereby improving the flexibility of the first section 100.

Figure 7:
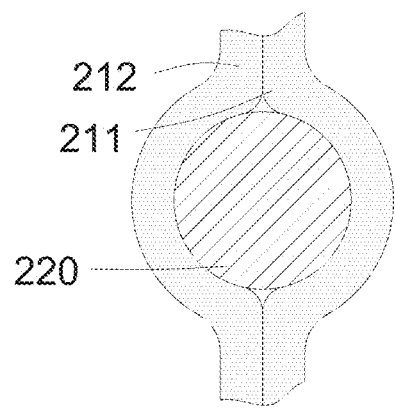
FIG. 7 is a partial schematic structural view of a second covering film of a second section of FIG. 2 matched with a second radial supporting structure.

Referring to FIG. 7, the second covering film 210 includes a second inner film 211 and a second outer film 212 attached to the second inner film 211, the second radial supporting structure 220 is located between the second inner film 211 and the second outer film 212, the second inner film 211 and the second outer film 212 are of long cylindrical structures, and the lengths of the second inner film 211 and the second outer film in the axial direction of the second radial supporting structure 221 are equal to the axial length of the second section 200, so that all second wavy rings 221 of the second radial supporting structure 220 are sandwiched between the second inner film 211 and the second outer film 212.

Figure 8:
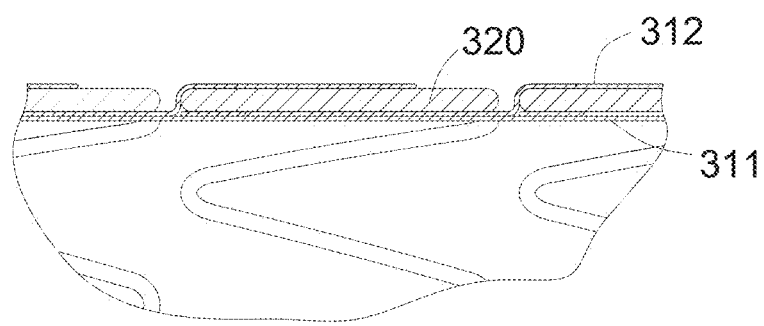
FIG. 8 is a partial schematic structural view of a third covering film of a transition section of FIG. 2 matched with a third radial supporting structure.

Referring to FIG. 8, the third covering film 310 includes a third inner film 311 and a number of third outer films 312 attached to the third inner film 311, the third radial supporting structure 320 is located between the third inner film 311 and the number of third outer films 312, and two ends of the third inner film 311 are connected with the first inner film 111 and the second inner film 211, respectively. The third inner film 311 is of a long cylindrical structure and the third outer films 312 are of short cylindrical structures, i.e. the length of the third inner film 311 in the axial direction of the third radial supporting structure 320 is greater than the lengths of the third outer films in the axial direction of the third radial supporting structure 320. Each third wavy ring 321 is sandwiched between a third inner film 311 and a third outer film 312, the crests of each third wavy ring 321 are exposed, and the troughs of each third wavy ring 321 are covered by the corresponding third outer film 312 and third inner film 311. For example, the entire third inner film 311 covers the inner side of the third radial supporting structure 320, one end of each third outer film 312 is disposed on the outer side of the corresponding third wavy ring 321, and the other end of the third outer film 312 extends to the inner side of the adjacent third wavy ring 321. For example, a portion of each third outer film 312 covers a ½ area of the outer side of its corresponding third wavy ring 321, i.e., each third outer film 312 covers from a middle position of the third wavy ring 321 on the inner side of the third outer film 312.

Figure 9:
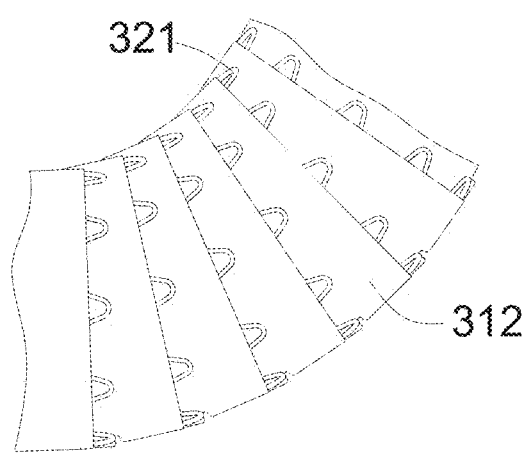
FIG. 9 is a schematic structural view of the transition section of FIG. 8 after being bent.

Referring to FIG. 9, since the crests or troughs of each third wavy ring 321 are exposed (that is, the crests or troughs of each third wavy ring 321 are not covered by the third outer films 312), the crests or troughs of each third wavy ring 321 can be separated from the third outer films 312 and the third inner film 311 (that is, the crests or troughs of each third wavy ring 321 can be titled relative to the third outer films 312 and the third inner film), such that when the transition section is bent, on a slightly bent side, in the two adjacent wavy rings 321, one third wavy ring 321 can be overlaid with another third wavy ring 321, so that the transition section 300 has a good bending property and is able to conform to the anatomical form of the blood vessel, and the transition section 300 is easily shortened and can better absorb the vibration and displacement transmitted by the first section 100, thereby ensuring that the second section 200 remains relatively stationary with respect to the branch blood vessel, and reducing the stimulation to the branch blood vessel wall by the second section 200. In the present application, the slightly bent side refers to a side where the bending radius is small when the transition section 300 is bent. In addition, since the crests of the slightly bent side are exposed outside, the crests of the slightly bent side do not easily penetrate through the third inner film 311 in a bending process, and the service life of the transition section 300 is prolonged.

It can be noted that in the present embodiment, the first inner film 111, the second inner film 211 and the third inner film 311 are integrally formed. That is, the first inner film 111, the second inner film 211 and the third inner film 311 are identical in material and size, and the first inner film 111, the second inner film 211 and the third inner film 311 are sequentially connected in the axial direction of the first tube body 101 to form a cylindrical structure.

According to the tube stent 10, when the radial length of the first section 100 is compressed by 50%, the radial supporting strength is 0.25 N/cm to 5 N/cm, so that the first section 100 is prevented from being extruded and deformed by the aortic stent when being in contact with the aortic stent, the sufficient supply of the blood flow to the branch blood vessel is effectively ensured. And at the same time the first section 100 has certain flexibility and shortening resistance, so that the first section 100 can conform more closely to the aortic wall and the aortic stent upon release, and the possibility of the risk that the opening of the tube stent 10 is covered by the aortic stent due to the retraction of the proximal end of the tube stent 10 caused by the flushing of the blood flow is low. The radial supporting strength of the second section 200 is less than the radial supporting strength of the first section 100, so that the distal end of the tube stent 10 is well anchored within the branch blood vessel and the stimulation of the second section 200 to the vessel wall can be controlled.

In addition, the transition section 300 has a better bending property and shortening property, so that the tube stent 10 can conform to various types of chimney operation methods and branch blood vessel approach anatomical forms, especially when used in the aortic arch, the aortic pulsation can be buffered by the transition section 300, and the vibration deformation of the tube stent 10 stays at the first section 100 and the transition section 300, thereby ensuring the relative stability of the second section 200 and the branch blood vessel, and reducing the stimulation to the branch blood vessel wall.

Embodiment 2

A tube stent 10a according to a second embodiment is mainly used for a branch blood vessel of a renal artery. A renal artery chimney technology mostly adopts a two-chimney technology. In order to ensure the patency of blood vessels of the renal arteries on both sides and reduce the compression on two chimneys by an abdominal aortic covered stent, what is different from Embodiment 1 is that, referring to FIG. 10, in the tube stent 10a, the tube diameter of a first section 100a is less than that of a second section 200a, and the transition section 300 is a tapered transition, that is, the transition section 300 is connected between the first section 100a and the second section 200a, and is of a truncated conical structure.

Figure 11:
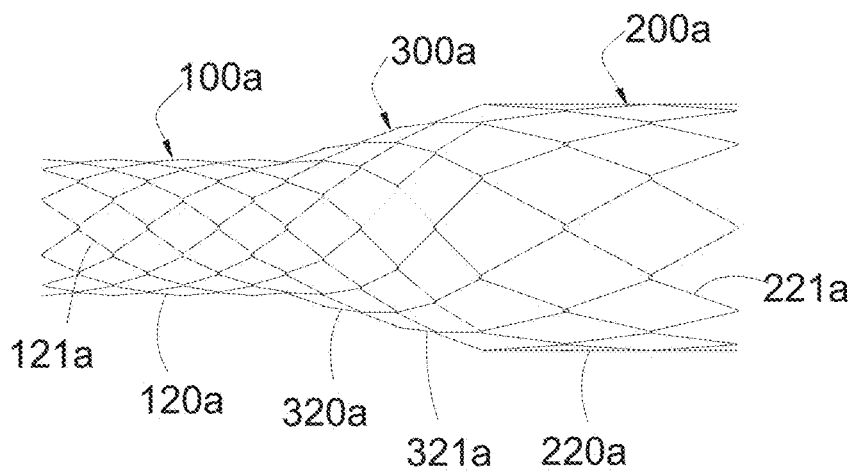
FIG. 11 is a schematic structural view of a bare stent of the tube stent of FIG. 10.
Figure 12:
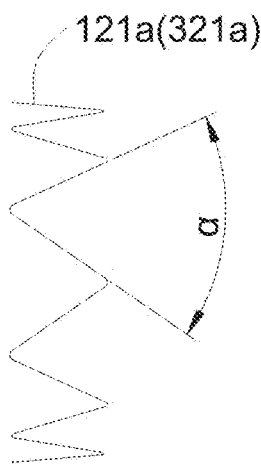
FIG. 12 is a schematic structural view of a first wavy ring or a third wavy ring of FIG. 11.
Figure 13:
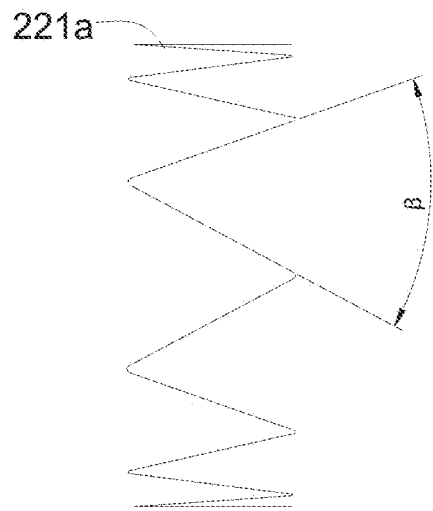
FIG. 13 is a schematic structural view of a second wavy ring of FIG. 11.

Referring to FIG. 11, structures of a first radial supporting structure 120a, a second radial supporting structure 220a and a third radial supporting structure 320a are similar to that of the second radial supporting structure 220 in Embodiment 1. That is, the first radial supporting structure 120a, the second radial supporting structure 220a and the third radial supporting structure 300a are woven using a single-layer weaving method. For example, a single-layer wave ring structure woven from a single nickel-titanium wire is used. A mesh structure of the first radial supporting structure 120a has a smaller pore diameter than a mesh structure of the second radial supporting structure 220a. Referring to FIGS. 12 and 13 together, the numbers of crests and troughs of a first wavy ring 121a, a second wavy ring 221a and a third wavy ring 321a are the same, and an included angle α between two adjacent side rods of each of the first wavy ring 121a and the third wavy ring 321a is the same and is greater than an included angle β between two adjacent side rods of the second wavy ring 221a, so that the radial supporting strength of the first section 100a and a transition section 300a is greater than the radial supporting strength of the second section 200a.

Figure 10:
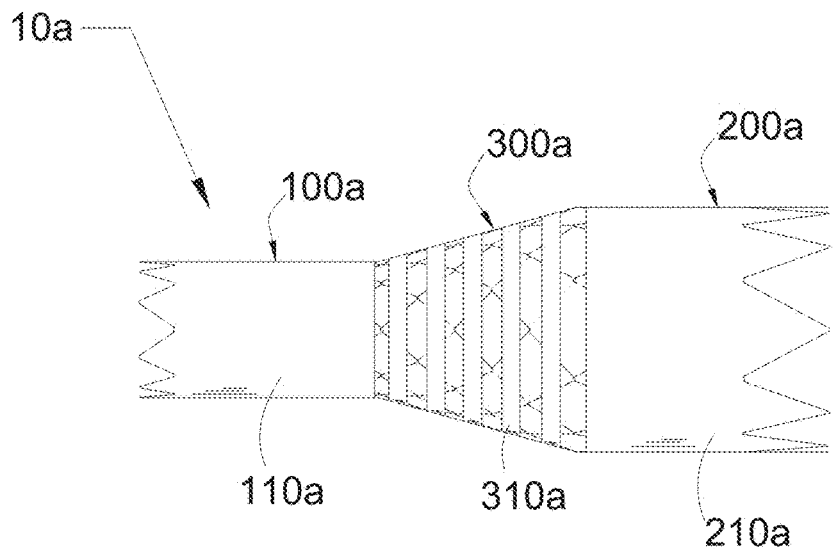
FIG. 10 is a schematic structural view of a tube stent according to a second embodiment.

With continuing reference to FIG. 10, a first covering film 110a and a second covering film 210a are the same in film covering method, and cover in the same manner as the second covering film 210 of the second section 200 in Embodiment 1, that is, the first covering film also includes a first inner film and a second outer film attached to the first inner film, the first inner film and the first outer film are also of long cylindrical structures, the axial lengths of the first inner film and the first outer film are equal to the axial length of the first section, the first wavy rings 121a are wrapped between the first inner film and the second outer film, and the second wavy rings 221a are wrapped between the second inner film and the second outer film.

Figure 14:
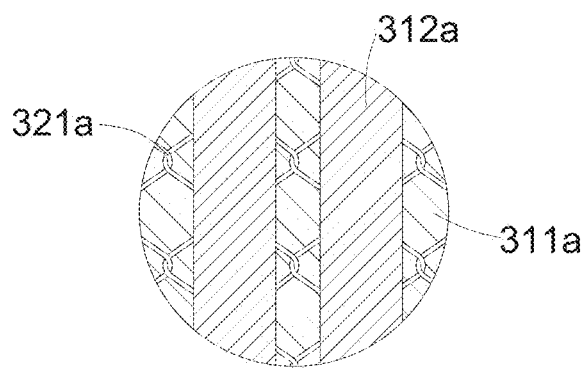
FIG. 14 is a partial schematic structural view of a third covering film of a transition section of FIG. 10 matched with the third radial supporting structure.

Referring to FIG. 14, the number of third outer films 312a is plural, and the third outer films 312a can cover rod bodies of third wavy rings 321a in circumferential directions of the third wavy rings 321a and expose the crests and troughs of the third wavy rings 321a. That is, each third outer film 312a covers middle areas of one row of third wavy rings 321a except for positions of the crests and the troughs. That is, the crests and troughs of each third wavy ring 321a are exposed, and the other positions of the third wavy ring 321a are covered by the third outer films 312a. Since the crests and troughs of each wavy ring 121 are exposed, it is possible to exert the characteristic that the two adjacent first wavy rings 321a in the third radial supporting structure 320a are close to each other, thereby enhancing the bending property and the shortening property of the transition section 300a. In one embodiment, the widths of the portions of the third outer films 321a in the circumferential directions are equal so that the transition section 300a can be bent in all directions to adapt to different vessel forms.

In one embodiment, the widths of the third outer films 312a in the axial direction of the transition section 300a are greater than or equal to ⅕ of the distance in the axial direction of the transition section 300a between the crest and the trough of the third wavy ring 321a clamped by the third outer films 312a, and less than or equal to ⅘ of the distance in the axial direction of the transition section 300a between the crest and trough of the third wavy ring 321a clamped by the third outer films 312a so as to ensure that no third wavy rings 321a clamped by the third outer films 312a can be separated from the covering films while the crests and troughs of the first wavy ring 321a can be exposed. In another embodiment, the widths of the third outer films 312a in the axial direction of the transition section 300a are equal to ½ of the distances in the axial direction of the transition section 300a between the crests and the troughs of the third wavy rings 321a clamped by the third outer films 312a so as to ensure that the transition section 300a has the better bending property and shortening property, and the structure of the transition section 300a can be stabilized.

Figure 15:
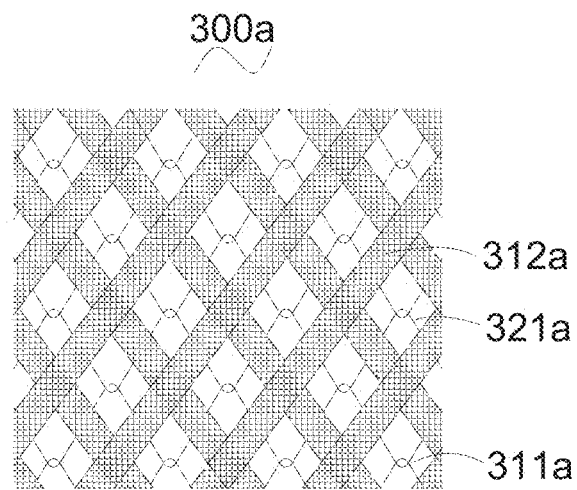
FIG. 15 is a partial schematic structural view of a third covering film of a transition section in another embodiment matched with the third radial supporting structure.

Further, the third outer films 312a may also cover the third wavy rings 321a in other directions along the third wavy rings 321a. Referring to FIG. 15, the angle between the extension direction of each third outer film 312a and the axial direction of the transition section 300a is not greater than 65°, so that the movable distance between the third wavy rings 321a is large, thereby improving the flexibility of the transition section 300a. In one embodiment, the angle between the extension direction of each third outer film 312a and the axial direction of the transition section 300a is 30° to 60°. In another embodiment, the angle between the extension direction of each third outer film 312a and the extension direction of the covered rod body is 90°±20°, so as to help the third outer film 312a cover as many third wavy rings as possible without changing the extension direction, thereby facilitating the film covering and the improvement of the production efficiency.

Further, all the rod bodies of the third wavy rings 321a are covered with the third outer films 312a to improve the stability of the film covering of the transition section 300a. Further, each third outer film 312a covers all of the third wavy rings 321a, that is, each third outer film 312a extends from the first third wavy ring 321a to the last third wavy ring 321a, the third outer film 312a covers at least one rod body of each third wavy ring 321a, and each third outer film 312a covers a longer area, so that the binding force between each third outer film 312a and the third inner film can be increased, the probability that the third outer film 312a is loosened can be reduced, the number of the third outer films 312a can be reduced, the difficulty of a film covering process is reduced, and the production efficiency is improved. In the present embodiment, during film covering, the third outer film 312a is pulled from the rod body position of the first third wavy ring 321a toward the rod body of the second third wavy ring 321a, and then toward the rod body of the third wavy ring 321a until the rod body of the last third wavy ring 321a so as to complete the film covering in one extension direction, then the film covering in a second extension direction is performed in the same manner, so that all rods bodies of all the third wavy rings 321a are covered with the third outer films 312a. Further, the widths of the portions of the third outer films 312a are equal, and the widths of the third outer films 312a are ⅓ to ½ of the lengths of the rod bodies of the third wavy rings 321a, so that the requirements that the shortening rate of the transition section 300a is between 30% and 50%, and the bending radius of the transition section 300a is less than 5 mm are met. Further, in other embodiments, the number of rod bodies covered by the third outer films 321a and the widths of the third outer films 321a may be adjusted accordingly to meet the required shortening rate and bending radius of the transition section 300a. For example, the third outer films 312a may cover only portions of the rod bodies or the widths of the number of third outer films 312a may be not exactly the same.

It can also be appreciated that the third inner film and the third outer film 312a may take other forms as well, for example, the third outer film 312a may be in the form of an integral film covering all of the third wavy rings 321a on outer surfaces of the third wavy rings 321a, the third inner film is of a strip structure covering the third wavy rings 321a only on inner surfaces of the third wavy rings 321a, only covering two third wavy rings 321a at the head end and the tail end (i.e. the first third wavy ring 321a close to the first section and the last wavy ring 321a close to the second section).

According to the tube stent 10a, the first section 100a adopts a single-layer weaving method, the included angle between two adjacent side rods of the first wavy ring 121a is large, and an inner film and outer film integral film covering mode is adopted, so that the radial supporting strength of the first section 100a is large, thereby ensuring that the first section 100a can be prevented from being extruded and deformed when being released in parallel with the abdominal aortic covered stent. Because the crests and the troughs of the third wavy ring 321a are exposed outside, the transition section 300a has a better bending property and shortening property, a better release form of the tube stent 10a can be ensured, and the influence of arterial pulsation on the second section 200a can also be eliminated. The included angle between two adjacent side rods of the second wavy ring 221a in the second section 200a is small, so that the second section 200a has small radial supporting strength; meanwhile, the second section 200a adopts the inner film and outer film integral film covering method, so that the second section 200a has high shorting resistance, thereby effectively improving the wall attaching property and stability of the second section 200a.

In addition, since the numbers of crests and troughs of the first wavy rings 121a, the second wavy rings 221a and the third wavy rings 321a are the same, the overall uniformity of the tube stent 10a is good, and uniform assembly and release of the tube stent 10a are facilitated.

Embodiment 3

Figure 16:
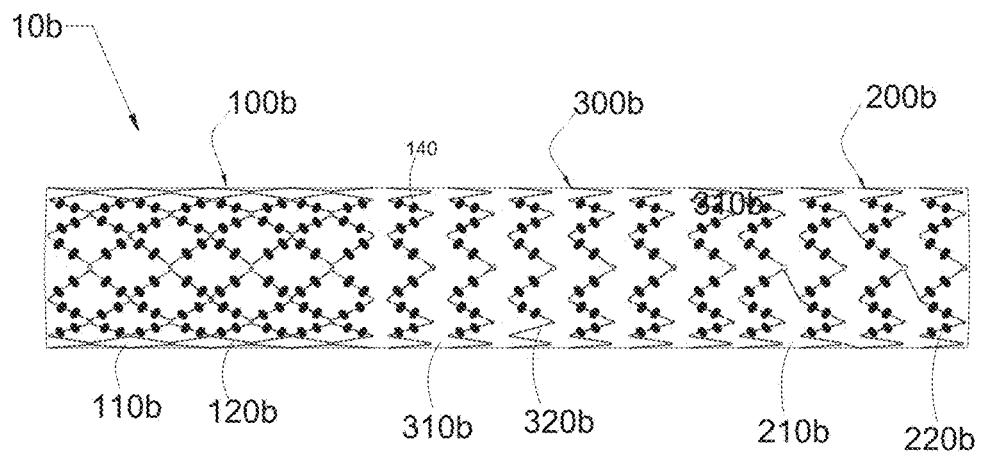
FIG. 16 is a schematic structural view of a tube stent according to a third embodiment.

Referring to FIG. 16, what is different from Embodiment 1 is that a bare stent of a tube stent 10b of a third embodiment is cut with a nickel-titanium tube, and covered with a single-layer film covering structure including only an inner film, for example, a PET inner film, to which the bare stent is fixed by sutures 140.

Figure 17:
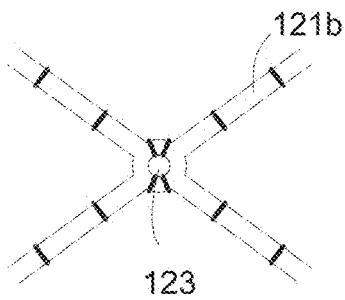
FIG. 17 is a partial schematic structural view of a first radial supporting structure of a first section of FIG. 16.

A first radial supporting structure 120b of a first section 100b is integrally cut and includes a mesh structure formed by connecting a number of first wavy rings 121b in the axial direction, so that the first section 100b is high in radial supporting strength and is not prone to bending deformation. In one embodiment, the first wavy ring 121b includes 5 to 20 crests and troughs. Referring to FIG. 17, in two adjacent first wavy rings 121b, a through hole 123 for sewing with a first covering film 110b is arranged at a connecting part of the crest of one first wavy ring 121b and the trough of the other wavy ring 121b.

A second radial supporting structure 220b of a second section 200b is likewise integrally cut and includes a number of connected second wavy rings 221b.

Figure 18:
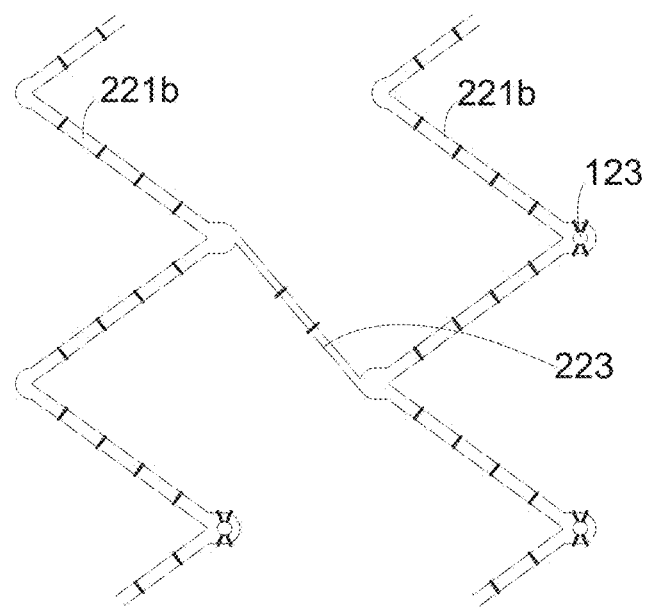
FIG. 18 is a partial schematic structural view of a second radial supporting structure of a second section of FIG. 16.

For example, referring to FIG. 18, the second radial supporting structure 220b includes a number of spaced apart second wavy rings 221b, where—the adjacent second wavy rings 221b are connected by a connecting rod 223. For example, the number of the connecting rods 223 between the two adjacent second wavy rings 221b is 1 to 10, so that the stability of the second section 200b is effectively guaranteed, the shortening rate of the second section 200b is reduced, and the risk of displacement when the second section 200b is anchored is reduced. In some examples, the second wavy ring 221b includes 5-20 crests and troughs.

It can be noted that positions of a portion of the crests of the second wavy ring 221b may also be provided with through holes 123 for sewing with a second covering film 210b.

A third radial supporting structure 320b of a transition section 300b is formed with a number of independent third wavy rings 321b in a cutting manner. For example, the third wavy ring 321b includes 5-20 crests and troughs.

Figure 19:
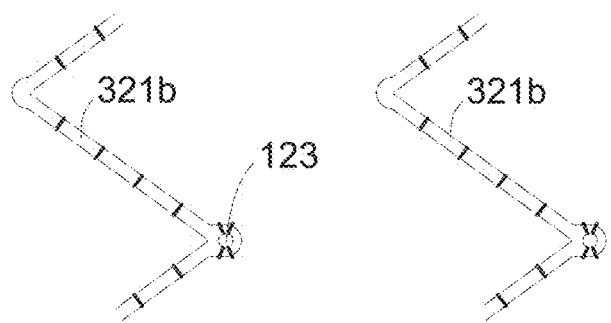
FIG. 19 is a partial schematic structural view of a third radial supporting structure of a transition section of FIG. 16.

Referring to FIG. 19 together, a phase difference between two adjacent third wavy rings 321b is zero, that is, a line connecting two nearest crests or two nearest troughs of the adjacent third wavy rings 321b is parallel to the axial direction of the transition section 300b. In this embodiment, the spacing between two adjacent third wavy rings 321b (that is, the distance in the axial direction between a trough of the first third wavy ring 321b of two adjacent third wavy rings 321b and a crest of the other third wavy ring 321b closest to the trough, viewed from the direction of the first section 100b to the second section 200b) is equal to ½ of the wave height of the third wavy ring 321b (the wave height refers to the vertical height between the crest and the trough of the third wavy ring 321b), in other words, the shortening rate of the transition section 300b is 30%. Further, in other embodiments, a ratio of the spacing between the two adjacent third wavy rings 321b to the wave height of the third wavy ring 321b may be other values as long as it is ensured that the shortening rate of the transition section 300b is not greater than 50%. In some examples, each crest or trough position of the third wavy ring 321b is provided with a through hole 123 for sewing with a third covering film 310b.

In this embodiment, the numbers of the crests and troughs of the first wavy ring 121b, the second wavy ring 221b and the third wavy ring 321b are equal, and the included angle between the wave height of each wavy ring and a rod body is equal, so that the consistency is good.

The first covering film 110b, the second covering film 210b and the third covering film 310b adopt integrally formed PET films, and the first radial supporting structure 120b, the second radial supporting structure 220b and the third radial supporting structure 320b are respectively fixed to the outer sides of the PET films by sutures. It can be appreciated that in other embodiments, the first radial supporting structure 120b, the second radial supporting structure 220b and the third radial supporting structure 320b may be fixed to the inner sides of the PET films by sutures, respectively. It can also be appreciated that in other embodiments, the first covering film 110b, the second covering film 210b and the third covering film 310b may also adopt integrally formed PTFE films or other similar films.

Figure 20:
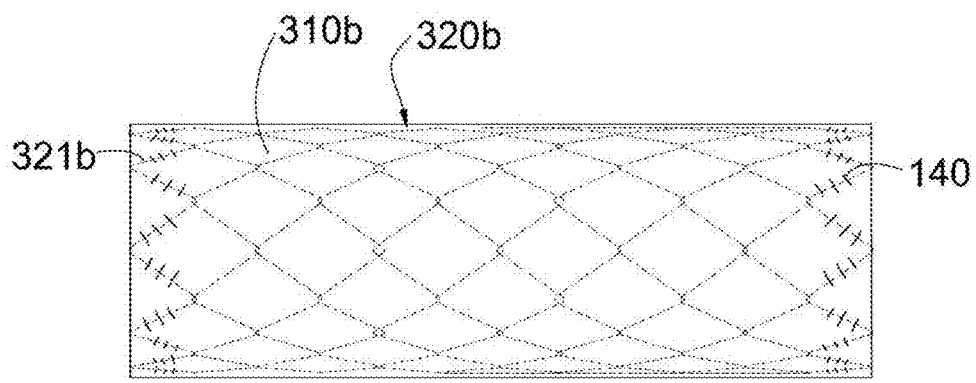
FIG. 20 is a schematic structural view of a transition section in another embodiment.

In this embodiment, all of the third wavy rings 321b in the third radial supporting structure 320b are fixed to the third covering film 310b by sutures. Further, in other embodiments, only a portion of the third wavy rings 321b are fixed to the third covering film 310b. For example, only the third wavy rings 321b at two ends are fixed to the third covering film 310b by sutures, and the remaining third wavy rings 321b are not fixedly connected with the third covering film 310b. Referring to FIG. 20, the transition section 300b includes a third radial supporting structure 320b and a third covering film 310b covering the third radial supporting structure 320b. The structure of the third radial supporting structure 320b may refer to the third radial supporting structure 320a in Embodiment 2, that is, the third radial supporting structure 320b includes a mesh structure formed by connecting a number of third wavy rings 321b in the axial direction, and the crests and troughs of two adjacent third wavy rings 321b are arranged opposite to each other and are buckled with each other to form an interlocking structure. The third covering film 310b is located on the outer side of the third radial supporting structure 320b (i.e., the third covering film 310 includes only an outer film and no inner film), only two third wavy rings 321b at the head and the end of the third radial supporting structure 320b are fixedly connected with the third covering film 320b by sutures 140, and the third wavy ring 321b in the middle is not fixed to the third covering film 310b. It can also be appreciated that a number of third wavy rings 321b may be fixed to the third covering film 310b by sutures as desired, for example, a number of third wavy rings 321b at the ends may be fixed to the third covering film 310b by sutures, leaving only a small portion of the third wavy rings 321b not connected with the third covering film 310b.

Embodiment 4

Figure 21:
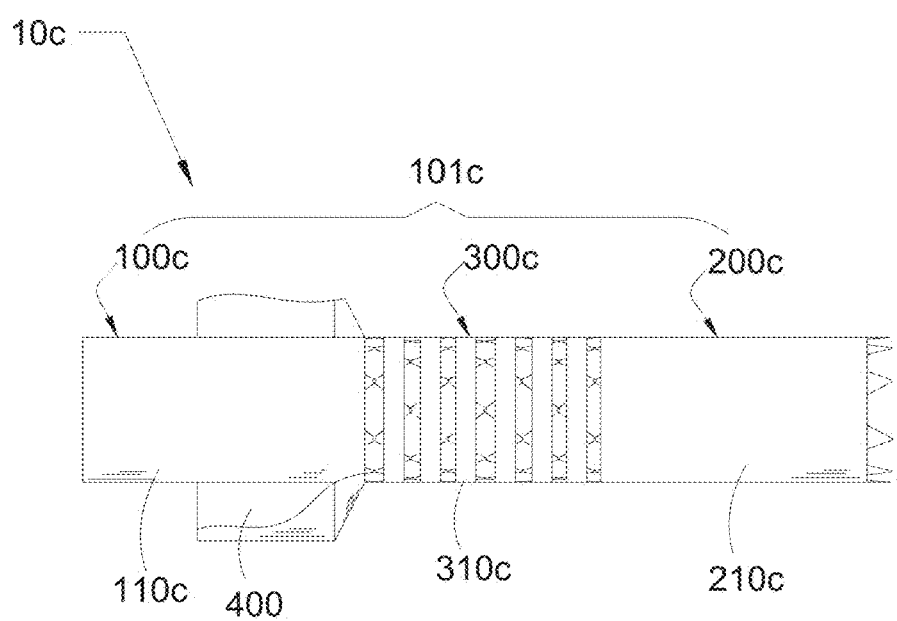
FIG. 21 is a schematic structural view of a tube stent according to a fourth embodiment.

Referring to FIG. 21, what is different from Embodiment 1 is that a tube stent 10c of a fourth embodiment further includes a second tube body 400 sleeving a first tube body 101c, and one end of the second tube body 400 is in sealing connection with the outer surface of the first tube body 101c. For example, the second tube body 400 is positioned at a first section 100c, with an opening of the second tube body 400 facing one end of the first tube body 101c far away from the second section. When blood flows into the tube stent 10c from the proximal end, the second tube body 400 can block a gap formed by the matching of the tube stent 10c and an aortic covered stent, thereby effectively preventing type I endoleak. In one embodiment, the length of the second tube body 400 is less than that of the first section 100c. In another embodiment, one end of the first section 100c far away from the second section 200c extends beyond an open end of the second tube body 400. For example, the end of the first section 100c far away from the second section 200c extends beyond the open end of the second tube body 400 by 10-15 mm, so that the tube stent 10c is better matched with the aortic covered stent, avoiding the occurrence of type I endoleak.

Figure 22:
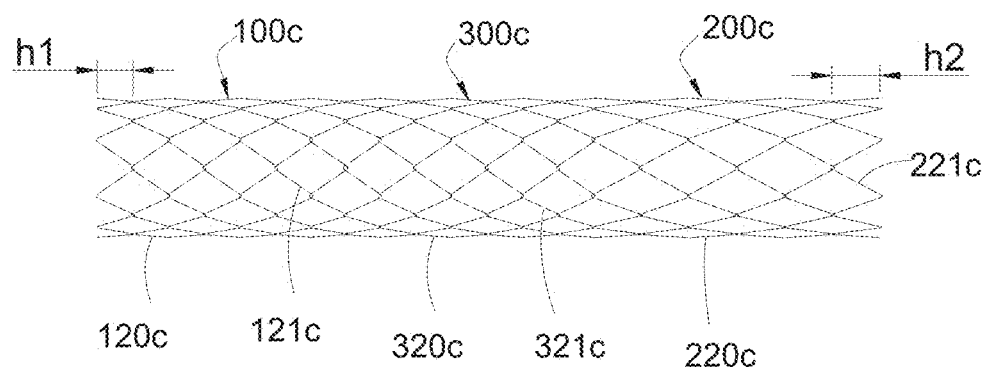
FIG. 22 is a schematic structural view of a bare stent of the tube stent of FIG. 21.

Referring to FIG. 22, a first radial supporting structure 120c, a second radial supporting structure 220c and a third radial supporting structure 300c are woven in a single-layer weaving method. For example, a single-layer wave ring structure woven from a single nickel-titanium wire is used. That is, structures of the first radial supporting structure 120c, the second radial supporting structure 220c and the third radial supporting structure 320c are similar to that of the second radial supporting structure 220 in Embodiment 1. The numbers of crests and troughs of the first wavy rings 121c, the second wavy rings 221c and the third wavy rings 321c are the same, and the wave heights h1 of the first wavy rings 121c and third wavy rings 321c are equal and are less than the wave heights h2 of the second wavy rings 221c, so that the radial supporting strength of the first section 100c is greater than that of the second section 200c.

In this embodiment, film covering methods of a first covering film 110c, a second covering film 210c and a third covering film 310c are the same as those of the corresponding portions in Embodiment 2, and thus will not be described in detail herein.

In order to allow the second tube body 400 to better block the gap created between the tube stent 10c and the aortic covered stent, for example, the radial supporting strength of the second tube body 400 is less than that of the first section. For example, a supporting structure of the second tube body 400 employs a nickel-titanium wire having a smaller wire diameter under the same other conditions. For example, the first tube body employs a nickel-titanium wire having a wire diameter of 0.0060-0.0080 inches, and the second tube body 400 employs a nickel-titanium wire having a wire diameter of 0.0045-0.0059 inches. In order to prevent the second tube body 400 from being displaced in the gap between the tube stent 10c and an artery covered stent, the second tube body 400 may adopt the same film covering method, namely the inner film and outer film integral film covering method, as the first section 100c, so that the second tube body 400 has relatively high shorting resistance and low flexibility, and the second tube body 400 is thus prevented from being displaced in the filling gap. For example, a thickness of the covering film of the second tube body 400 is less than that of the covering film of the first section 100c to facilitate the loading of the tube stent 10c into a sheath tube and reduction of an inner diameter of the sheath tube required for containing the sheath.

According to the tube stent 10c, the second tube body 400 is arranged at the periphery of the first tube body 101c, and the radial supporting strength of the second tube body 400 is less than that of the first tube body, so that the tube stent 10 is prevented from further compressing the artery covered stent in an extrusion process with the artery covered stent, to further avoid the increase of the gap between the tube stent 10c and the artery covered stent and at the same time better fill the gap between the tube stent 10c and the artery covered stent, thereby effectively preventing internal hemorrhage.

Embodiment 5

Figure 23:
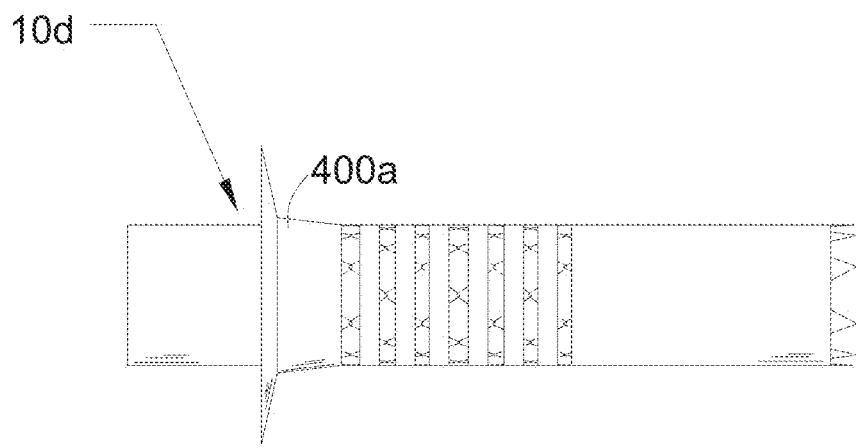
FIG. 23 is a schematic structural view of a tube stent according to a fifth embodiment.
Figure 24:
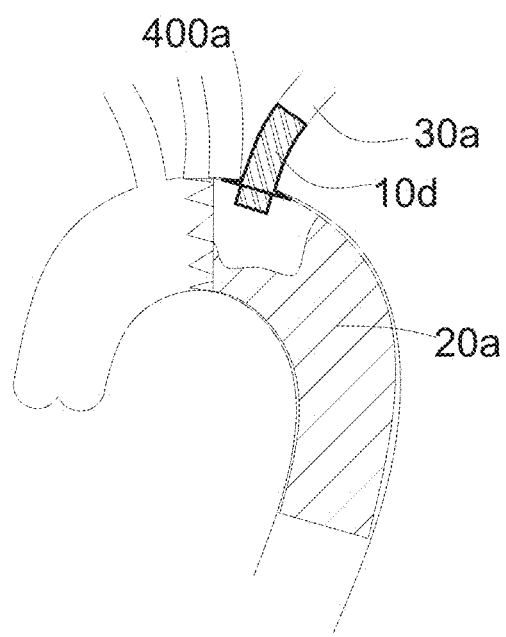
FIG. 24 is a schematic structural view of the tube stent of FIG. 23 implanted into a lumen in cooperation with a main stent.

Referring to FIG. 23, a tube stent 10d of a fifth embodiment is different from that of Embodiment 4 in that the second tube body 400a can be outwardly bent. Referring to FIG. 24 together, the tube stent 10d corresponds to another release form, and after a main stent 20 is fenestrated, a proximal end of the tube stent 10d is anchored to a lumen of the main stent 20a through a window, and a distal end of the tube stent 10d is located outside the main stent 20a and anchored in a branch blood vessel 30a. After entering the main stent 20a, the second tube body 400a is turned outwards and attached to the inner side of the main stent 20a to prevent a blood flow from leaking from the window position of the main stent 20a.

Embodiment 6

Figure 25:
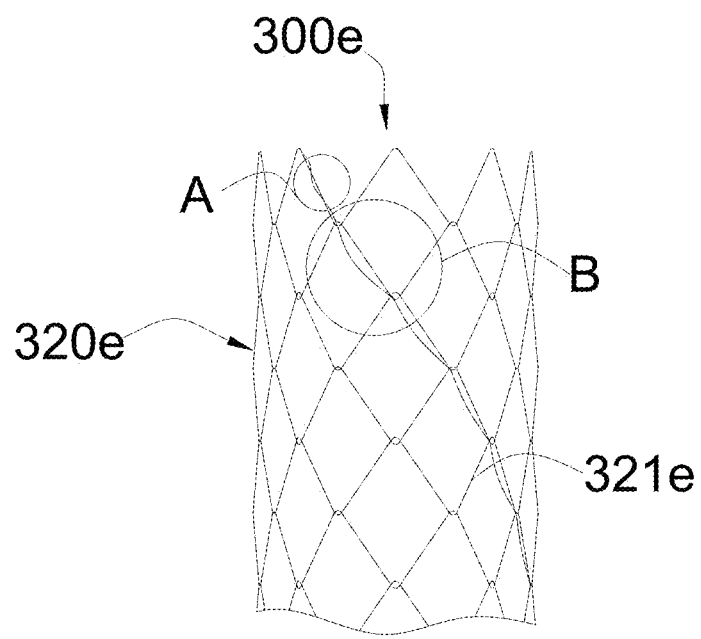
FIG. 25 is a schematic structural view of a transition section according to a sixth embodiment without being covered.
Figure 26:
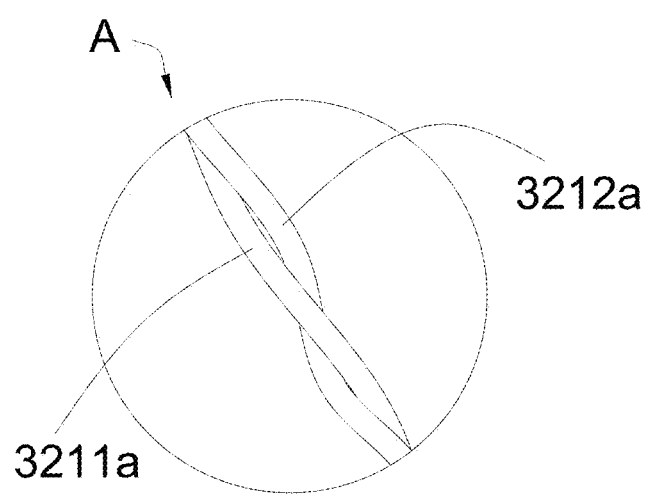
FIG. 26 is an enlarged view of a portion A of FIG. 25.
Figure 27:
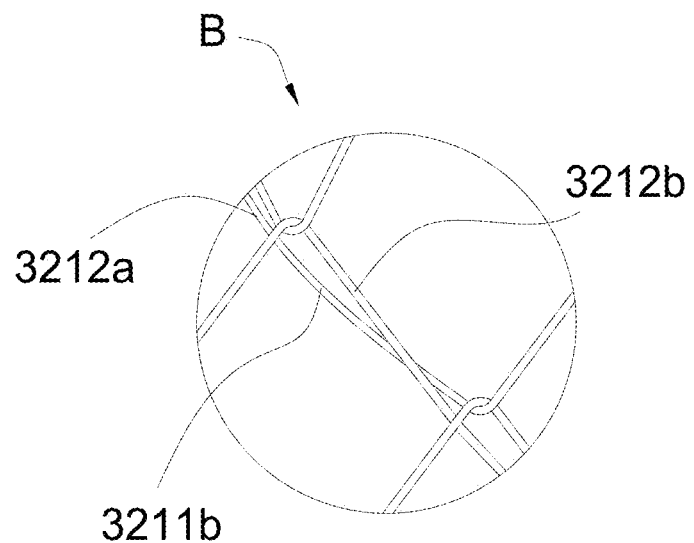
FIG. 27 is an enlarged view of a portion B of FIG. 25.

Referring to FIG. 25, what is different from Embodiment 1 is that a third radial supporting structure 320e of a transition section 300e of a tube stent of a sixth embodiment is continuously woven with a single wire. For example, the third radial supporting structure 320e includes a number of third wavy rings 321e sequentially arranged in the axial direction, the number of third wavy rings are connected in the axial direction to form a mesh structure, crests and troughs of two adjacent third wavy rings 321e are arranged opposite to each other and are mutually buckled to form an interlocking structure, the number of third wavy rings 321e are woven from the first third wavy ring 321e to the last third wavy ring 321e of the transition section 300e by a same metal wire, and the wire head and the wire tail of at least one the third wavy ring 321e are wound no more than twice and span to the next third wavy ring 321e. Referring to FIGS. 26 and 27 together, a wire head 321a and a wire tail 3212a of the first third wavy ring 321e of the transition section 300e are fixed by a number of times of winding as seen from the top down, after the first wavy ring 321e is woven, the wire tail 321a of the first wavy ring 321e obliquely spans to the second third wavy ring 321e in the direction of the wire head 321a, and acts as a wire head 3211b of the second third wavy ring 321e to undergo the weaving of the second third wavy ring 321e, after the second third wavy ring 321e is woven, a wire tail 3212b presses the wire head 321b to improve the stability of the structure, that is, the wire head 3211b and the wire tail 3212b are wound (inserted) by one time, then the wire tail 3212b obliquely spans to the third wavy ring 321e in the direction of the wire head 3211b, the method of the second third wavy ring 321e is repeated until the last third wavy ring 321e is woven, and then the last wire tail is fixed to rod bodies of the corresponding third wavy ring 321e by a number of times of winding. With the adoption of the weaving structure, due to the fact that the metal wires of the two adjacent third wavy rings 321e have high degrees of freedom, the flexibility of the transition section 300e can be improved advantageously. In addition, the single wire is adopted for continuous weaving, and the whole transition section 300e is only provided with two ends of the wire head and the wire tail, thereby reducing the influence of the wire head and the wire tail on the vessel wall to a great extent.

It can be noted that in the weaving process, except that the wire heads and the wire tails of the first and last third wavy rings 321e are fixed through a number of times of winding, the wire heads and the wire tails of the other third wavy rings 321e can be wound (inserted) by one or two times to ensure the stability of the wire heads and the wire tails. At the same time, it is also ensured that the relative displacement of the adjacent third wavy rings 321e is prevented from being limited due to a large number of winding times.

It can be appreciated that in other embodiments, the third wavy rings 321e of the transition section 300e are not so limited, e.g., the wire head and tail of the first third wavy ring 321e may be fixed by winding, the wire head and tail of the second third wavy ring 321e may be wound only one time, and the wire head and wire tail of the third wavy ring 321e may be wound at least two times, and the number of winding times may be adjusted according to the required flexibility of the transition section 300e.

It can also be appreciated that the third radial supporting structure 320e of the transition section 300e may also employ a number of metal wires to form a corresponding multi-layer woven structure, such as two metal wires to form a double-layer woven structure, which is similar to the first radial supporting structure of Embodiment 1.

Embodiment 7

Figure 28:
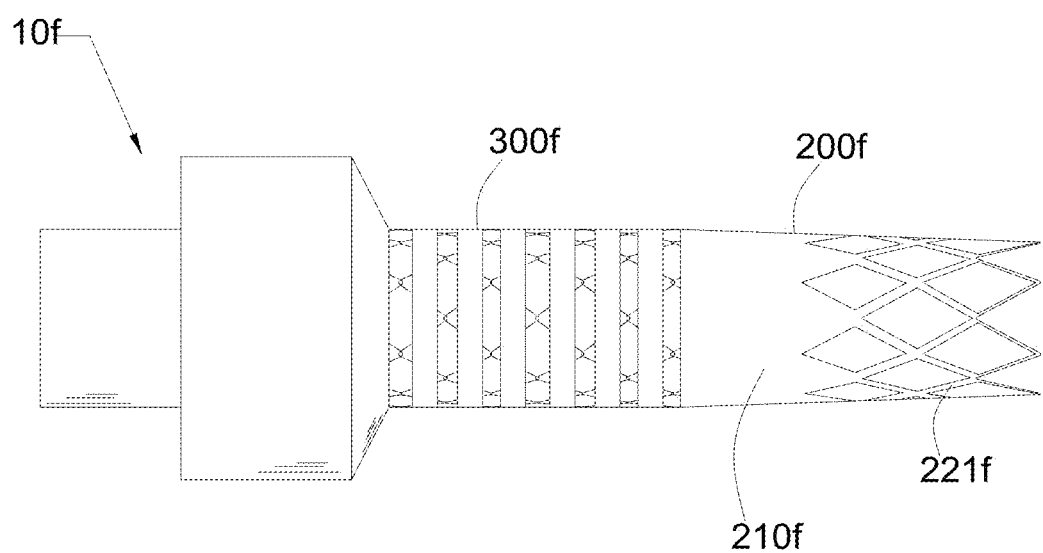
FIG. 28 is a schematic structural view of a tube stent according to a seventh embodiment.

Referring to FIG. 28, what is different from Embodiment 4 is that the diameter of the end, close to a transition section 300f, of a second section 200f of a tube stent 10f of Embodiment 7 is greater than that of the end, far away from the transition section 300f, of the second section 200f. For example, the second section 200f is a frustum-shaped structure, and a difference value between the diameter of the end, close to the transition section 300f, of the second section 200f and the diameter of the end, far away from the transition section 300f, of the second section 200f is 1-3 mm to better conform to the anatomical form of the branch blood vessel.

Further, a second covering film 210f at the end, far away from the transition section 300f, of the second section 200f is provided with a hollow structure, and the hollow structure is located in an area where the second covering film 210f is not in contact with a second supporting structure (not shown), that is, the second covering film 220f is hollowed out on the second covering film 210f along the pattern of the second supporting structure, so that a distal end of the tube stent 10f can be prevented from shielding a branch blood vessel. In the illustrated embodiment, a number of diamond-shaped hollow structures are provided on the covering film at the end, far away from the transition section 300f, of the second section 200f, and the number of diamond-shaped hollow structures are uniformly distributed in the circumferential direction. In this embodiment, the hollow structure arranged at the end, far away from the transition section 300f, of the second section 200f is 12-18 mm in length, for example 15 mm in length. For example, in this embodiment, an area on the second covering film 210f where the hollow structure is provided cover three second wavy rings 221f. It can be noted that the hollow structure can be arranged as desired, for example, the hollow structure can also be selectively arranged at certain specific locations without covering the entire circumferential direction, and the hollow area can also be non-uniformly distributed in the circumferential direction.

It can be appreciated that in other embodiments, the end, far away from the transition section 300f, of the second section 200f may not be provided with the second covering film 210f.

Embodiment 8

Figure 29:
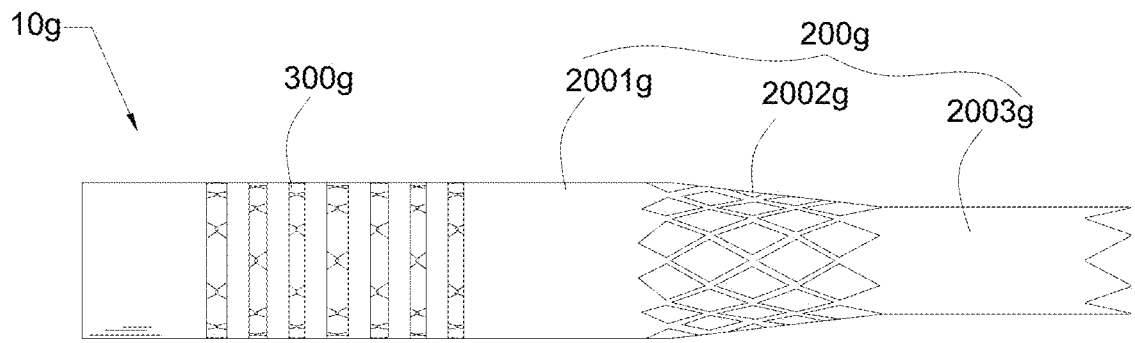
FIG. 29 is a schematic structural view of a tube stent according to an eighth embodiment.

Referring to FIG. 29, what is different from Embodiment 7 is that a second section 200g of a tube stent 10g of an eighth embodiment includes a connecting section 2001g, a tapered section 2002g and a distal section 2003g, two ends of the tapered section 2002g are connected with the connecting section 2001g and the distal section 2003g, respectively. The end, far away from the tapered section 2002g, of the connecting section 2001g is connected with a transition section 300g. The diameter of the end, close to the connecting section 2001g, of the tapered section 2002g is greater than the diameter of one end, close to the distal section 2001g, of tapered section 2002g. For example, the end, close to the connecting section 2001g, of the tapered section 2002g, the connecting section 2001g and the transition section 300g are equal in diameter, the diameter of the distal section 2003g is equal to that of the end, far away from the connecting section 2001g, of the tapered section 2002g, and the diameter of the distal section 2003g is ⅓ to ¾ of the diameter of the connecting section 2001g. The taper section 2002g is provided with a hollow structure. In this embodiment, the diameter of the distal section 2003g is ½ the diameter of connecting section 2001g.

Figure 30:
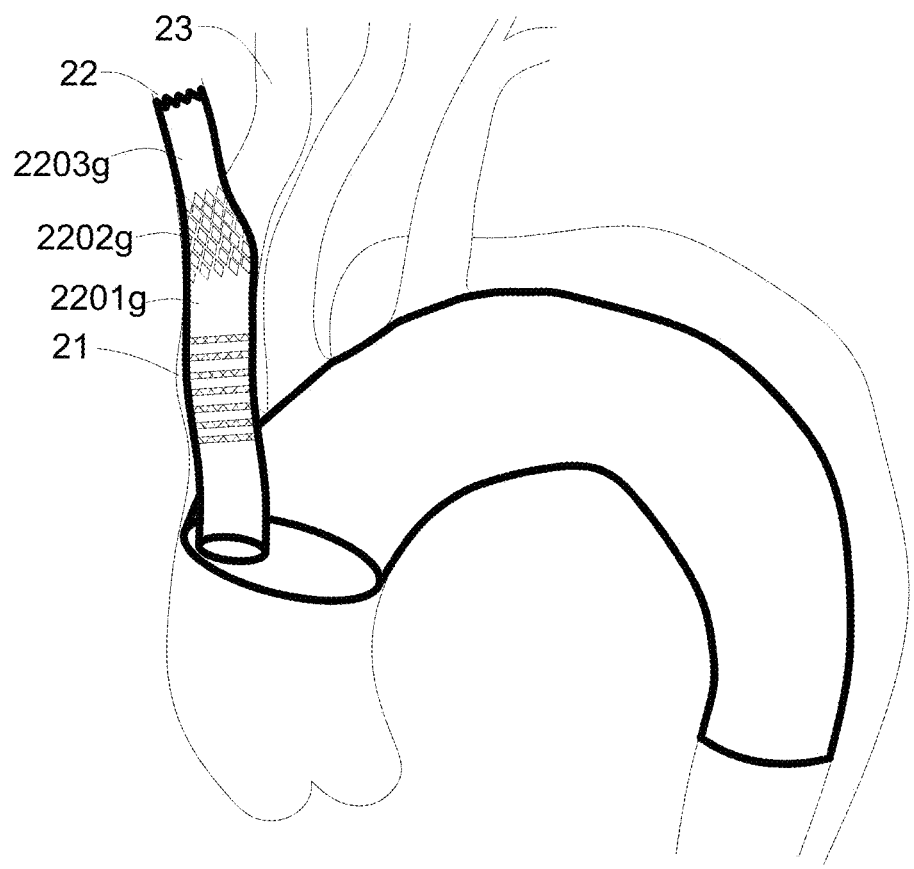
FIG. 30 is a schematic structural view of the tube stent shown in FIG. 29 after implantation into a blood vessel.

Referring to FIG. 30 together, when the tube stent 10g needs to be anchored to a branched innominate artery 21, and a right subclavian artery 22 has a relatively close opening, i.e., the innominate artery 21 is relatively short, after implantation of the tube stent 10g, the hollow structure of the tapered section 2002g can effectively ensure the patency of the blood flow of a left common carotid artery 23, and the diameter difference between the connecting section 2001g and the distal section 2003g enables the tube stent 10g to be well attached to the right subclavian artery 22 on the premise of less stimulation to the vessel wall, thereby preventing the tube stent 100g from being displaced.

It can be noted that the first radial supporting structure, the second radial supporting structure, the third radial supporting structure, the first covering film, the second covering film, and the third covering film are not limited to the structures employed in the embodiments described above. Other structures may also be used where conditions are met. Furthermore, the first radial supporting structure, the second radial supporting structure and the third radial supporting structure in each embodiment are not uniquely fixed to the first covering film, the second covering film and the third covering film. Mutual combination and collocation can be carried out when conditions are met. For example, the first radial supporting structure in Embodiment 1 may employ the first covering structure in Embodiment 1 or the first covering structure in Embodiment 2.

The various technical features of the above-mentioned embodiments can be combined in any way. In order to simplify the description, not all possible combinations of the various technical features of the above-mentioned embodiments are described. However, as long as there is no contradiction between these technical features, they should be considered as the scope of disclosure contained in this specification.

Some embodiments have been illustrated by the above-described embodiments, the description of which is specific and detailed, but should not be construed to limit the scope of the application. It should be noted that several variations and modifications may be made by those of ordinary skill in the art without departing from the spirit of the application, which fall within the scope of the application.

The invention claimed is:

1. A tube stent, comprising:
a first tube body, the first tube body comprising a first section, a second section and a transition section which is positioned between the first section and the second section, one end of the transition section is connected with the first section, the other end of the transition section is connected with the second section, and shortening rates of the first section and the second section are less than a shortening rate of the transition section, wherein the shortening rate of the transition section is greater than or equal to 30% and less than or equal to 50%.

2. The tube stent of claim 1, wherein a bending radius of the transition section is not greater than 10 mm.

3. The tube stent of claim 1, wherein an axial length of the transition section is not greater than ¾ of the total length of the first tube body.

4. The tube stent of claim 1, the first tube body further comprising a covering film and a bare stent connected with the covering film, the covering film comprises a first covering film arranged on the first section, a second covering film arranged on the second section and a third covering film arranged on the transition section, and the bare stent comprises a first radial supporting structure arranged on the first section, a second radial supporting structure arranged on the second section and a third radial supporting structure arranged on the transition section, the first radial supporting structure is connected with the first covering film, the second radial supporting structure is connected with the second covering film, and the third radial supporting structure is connected with the third covering film.

5. The tube stent of claim 4, wherein the second covering film at one end, far away from the transition section, of the second section is provided with a hollow structure.

6. The tube stent of claim 4, the third covering film comprising a third inner film and a plurality of third outer films attached to the third inner film, a length of the third inner film in the axial direction of the third radial supporting structure is greater than a length of the third outer film in the axial direction of the third radial supporting structure, the third radial supporting structure comprises a plurality of third wavy rings sequentially arranged in the axial direction of the first tube body, the third wavy rings comprise crests, troughs, and rod bodies each connecting two adjacent crest and trough, the rod bodies of the third wavy rings are clamped between the third inner film and the third outer films, and the crests or the troughs of the third wavy rings are exposed outside.

7. The tube stent of claim 6, wherein the third outer films cover the rod bodies of the third wavy rings in circumferential directions of the third wavy rings, and expose the crests and the troughs of the third wavy rings.

8. The tube stent of claim 7, wherein a plurality of the third wavy rings are connected in an axial direction to form a mesh structure, and the crests and the troughs of two adjacent third wavy rings are arranged opposite to each other and are buckled with each other to form an interlocking structure.

9. The tube stent of claim 6, wherein an angle between an extension direction of the third outer film and an axial direction of the transition section is not greater than 65°.

10. The tube stent of claim 9, wherein a width of each portion of the third outer film is equal, and a width of the third outer film in the axial direction of the third section is ⅓ to ½ of a height in the axial direction of the third section between the crest and the trough of the third wavy ring.

11. The tube stent of claim 1, wherein the diameter of one end, close to the transition section, of the second section is greater than the diameter of one end, far away from the transition section, of the second section.

* * * * *